United States Patent [19]
Steinberg

[11] Patent Number: 5,839,441
[45] Date of Patent: Nov. 24, 1998

[54] MARKING TUMORS AND SOLID OBJECTS IN THE BODY WITH ULTRASOUND

[75] Inventor: Bernard D. Steinberg, Wyndmoor, Pa.

[73] Assignee: The Trustees of the University of Pennsylvania, Philadelphia, Pa.

[21] Appl. No.: 657,412

[22] Filed: Jun. 3, 1996

[51] Int. Cl.⁶ ...................................................... A61B 8/00
[52] U.S. Cl. ..................................... 128/660.04; 128/898
[58] Field of Search ........................ 128/660.04, 660.06, 128/660.07, 660.08, 660.09, 660.1, 661.01, 660.01, 898

[56] References Cited

U.S. PATENT DOCUMENTS

| | | | |
|---|---|---|---|
| 5,040,225 | 8/1991 | Gouge | 128/660.04 |
| 5,524,636 | 6/1996 | Sarvazyan et al. | 128/660.01 |

OTHER PUBLICATIONS

Steinberg, "Target Detection–Sensitivity Enhancement Using High–Resolution Radar and 2–D and 3–D Stereo Target Displays." *IEEE Trans. AES*, Vo. 28, No. 3, Jul. 1992, pp. 886–890.

Perlow, et al., "Enhanced Target Dection Using Steroscopic Imaging Radar," *IEEE Trans. AES*, vol. 31, No. 3, Jul. 1995, pp. 1139–1148.

Steinberg, "Microwave Imaging of Aircraft," *Proc. IEEE*, vol. 76, No. 12, Dec. 1988, pp. 1578–1591.

Perlow, et al., "Automatic Stereo Processing of High Resolution Radar Imagery," *IEEE Trans. AES*, Apr. 1995, pp. 1–20.

*Primary Examiner*—George Manuel
*Attorney, Agent, or Firm*—Woodcock Washburn Kurtz Mackiewicz & Norris LLP

[57] ABSTRACT

A technique for subspeckle visibility in ultrasound imaging by using the speckle signatures to differentiate soft tissue from dense tissue and solid or compact objects. The information provided by a disparity mapper is used to automatically mark or tag these objects based on the observation that slight natural motion in soft tissue, as caused by breathing or probe compression, changes the details of a speckle pattern. This results from differential displacements among scatterers which alter the phase relations between their scattered fields. A small, compact object is displaced and distorted less, implying that its reflectivity pattern should be relatively stable, as compared to the fluctuating background reflectivity. This difference in the way the speckle patterns respond to body motion is detected by the disparity mapper. The output of the disparity mapper serves a marker or tag of dense tissue such as tumors or compact objects such as bits of shrapnel. Such techniques may be used by trained hospital sonographers and physicians to improve the location and identification of tumors and foreign objects in the tissue of a patient.

9 Claims, 8 Drawing Sheets

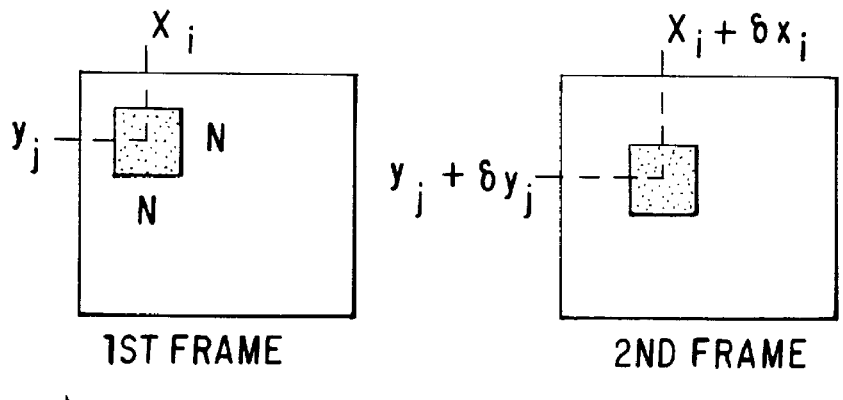
FIG. 2
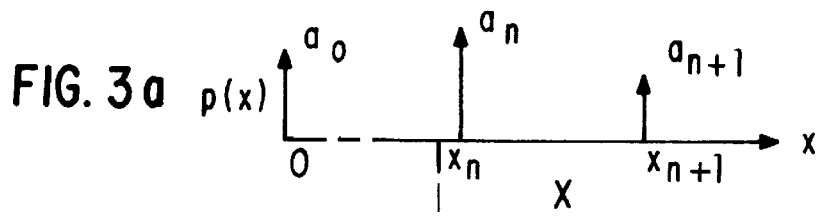
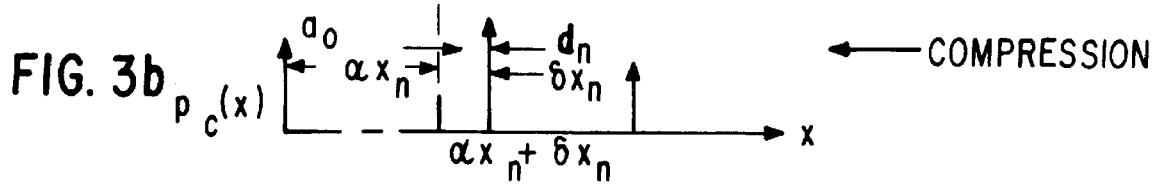
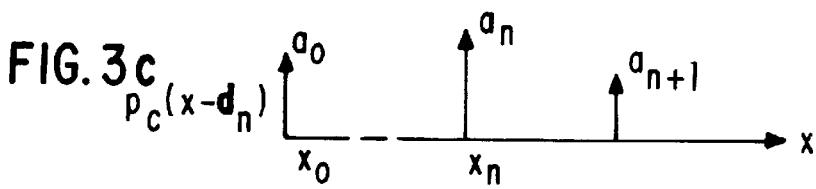

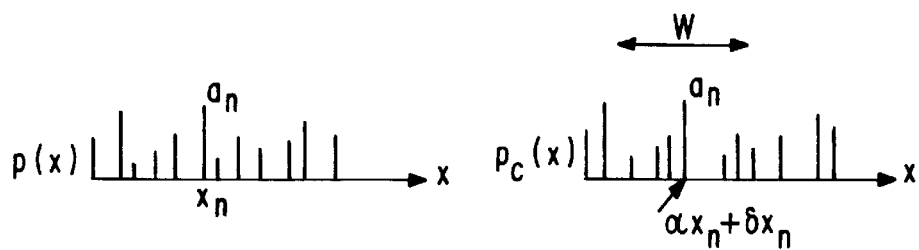
FIG. 4a
FIG. 4b
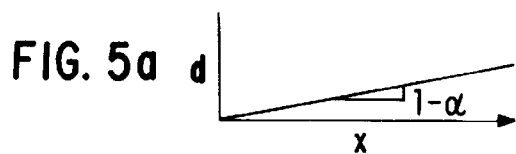
FIG. 5a
x = DISTANCE FROM ANCHOR
d = DISPARITY AT DISTANCE x
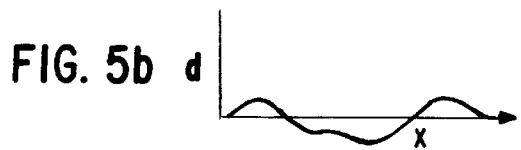
FIG. 5b
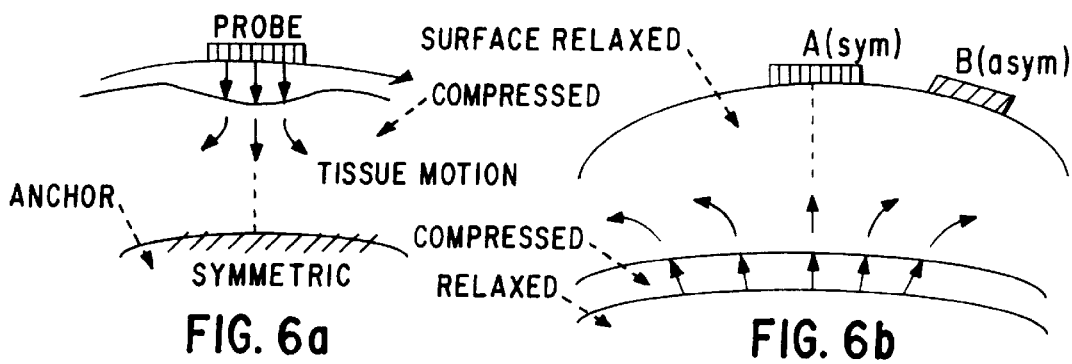
FIG. 6a
FIG. 6b
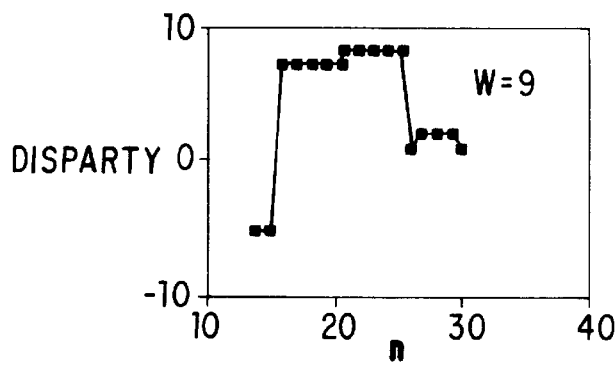
FIG. 8

MARKING TUMORS AND SOLID OBJECTS IN THE BODY WITH ULTRASOUND

BACKGROUND OF THE INVENTION

1. Field of the Invention

The present invention relates to an ultrasonic imaging system, and more particularly, to an ultrasonic imaging system which materially improves the detectability of dense tissue (such as tumors) and other foreign materials in a patient by rapidly discriminating between soft tissue and tumors as well as shrapnel and other small rigid parts. Such discrimination is based upon differences in how the speckle signatures of soft tissue and dense or rigid bodies vary with time in response to breathing or probe compression.

2. Description of the Prior Art

In imaging systems in which the image is derived from radiation back scattered from a target, such as medical ultrasound, underwater acoustic imaging, and radar, the resolution of the imaging is usually limited by the ability of the imaging system to distinguish the radiation echoed by the target from other random radiation or "noise" received from other objects in the aperture. Providing acceptable contrast of images of isolated targets in intrinsically low contrast imagery such as an aircraft submerged in ground clutter has been a particular problem. To address such problems in radar systems, the present inventor and others have developed a technique of disparity mapping during a radar study of 3-D high resolution stereo imagery which was found to augment target contrast and to enhance its detectability in clutter. Disparity mapping was found to be a useful means for providing excellent contrast of images of isolated targets in intrinsically low contrast imagery, such as aircraft submerged in ground clutter. For example, FIG. 1a illustrates a high resolution radar image of a Boeing 727 flying into Philadelphia International Airport. The radar data were taken at 3 cm wavelength and 150 MHZ bandwidth by a VFRC radio camera. The aircraft was at 3 km and at an elevation of 30 degrees. The resolution cell is approximately 1×1 m². FIG. 1b shows the airplane embedded in radar ground clutter from a soybean field. The target and the clutter data were obtained in separate experiments and were combined in such a way that the TCR (target-to-clutter ratio) can be controlled by a weighted coherent addition to their in phase and quadrature components, respectively. This is done in FIG. 1b in which the TCR is 3 dB. A second combined image is constructed in FIG. 1c which is an emulation of the same scene 100 ms later, after the aircraft would have flown a short distance. It was made by displacing the target horizontally by 3 pixels. The target is barely visible in FIGS. 1b and 1c but is readily detectable and recognizable in the 2-D disparity map of FIG. 1d, which is a two-dimensional disparity map derived from the images in FIGS. 1b and 1c. As illustrated in FIG. 1d, disparity mapping provides a target that is clearly visible, with high contrast.

High contrast resolution is also a requisite in ultrasound imaging for speedy detection and localization of targets such as tumors and foreign objects. To maximize patient safety, tumors should be detected at about 2 mm. Unfortunately, because of background clutter, sometimes tumors larger than 2 mm and small metal objects are invisible per se in B-scans. Ultrasound contrast resolution is affected by many factors, among which is speckle, which sets a high background "noise" level in the image. As a result, contrast resolution becomes a limiting factor in high quality echo ultrasound. While ultrasound contrast resolution is excellent relative, for example, to x-ray imagery, it nevertheless has a limiting level set by speckle. Speckle results from coherent interference in the back scatter or reradiation from the diffuse scattering centers of soft tissue (often called Rayleigh scattering). The coherent sum of the back scattered fields is the diffraction pattern of reradiating scatterers. This diffraction pattern is the radiation field sensed by the transducer. The additions and subtractions of the reradiation fields from the scattering centers give bright highlights and deep blacks. This spatial fluctuation in the B-scan image is a spatial "noise" which sets a limit to the weakest, and therefore typically the smallest, target that can be detected.

Many "contrast enhancement" techniques which rely upon echo intensity are known in the art; however, none of the known techniques to date provide sufficient contrast of images of isolated targets in intrinsically low contrast imagery, such as where it is necessary to distinguish soft tissue from dense tissue and solid or compact objects. As a result, it has been difficult to rapidly detect and localize targets within the aperture. Indeed, contrast resolution is usually a limiting factor in wave propagation based imaging systems. The present invention is accordingly designed to provide an improved contrast enhancement technique which permits the rapid marking of objects within the aperture.

SUMMARY OF THE INVENTION

The present invention provides a technique for subspeckle visibility in ultrasound imaging by using the speckle signatures to differentiate soft tissue from dense tissue and solid or compact objects. The information provided by a disparity mapper is used to automatically mark or tag these objects. In particular, the invention is based on the observation that slight natural motion in soft tissue, as caused by natural breathing or probe compression, changes the details of a speckle pattern. This results from differential displacements among scatterers which alter the phase relations between their scattered fields. A small, compact object is displaced and distorted less, implying that its reflectivity pattern should be relatively stable, as compared to the fluctuating background reflectivity. In accordance with the techniques of the invention, this difference in the way the speckle patterns respond to body motion is detected by a disparity mapper. The output of the disparity mapper serves a marker or tag of dense tissue such as tumors or compact objects such as bits of shrapnel.

The present invention thus relates to a method of identifying tumors and foreign materials in soft tissue of a patient using ultrasound imaging. In particular, the method of the invention aids the diagnostician in identifying tumors and foreign materials in soft tissue of a patient by performing the steps of imaging a target soft tissue area to obtain a first ultrasonic image; displacing the target soft tissue area; imaging the displaced target soft tissue area to obtain a second ultrasonic image; and identifying whether tumors or foreign materials are present in the target soft tissue area based on changes in a speckle pattern between the first and second ultrasonic images. In accordance with the method of the invention, the displacement may be obtained by compressing the target soft tissue area with a probe or, for the case of the imaging of a patient's breast tissue, for example, the necessary displacement may be obtained by waiting a predetermined interval of time during the patient's breath cycle whereby displacement of the breast tissue is caused by the patient's breath cycle.

In accordance with the preferred embodiment of the invention, the identifying step comprises the step of generating a disparity map of speckle signatures of the first and second ultrasonic images and marking the tumors or foreign materials in one of the first and second images using the disparity map. The marking can be accomplished by marking points displaced between the first and second ultrasonic images with a first pixel intensity in the disparity map, marking points which are minimally displaced between the first and second ultrasonic images with a second pixel intensity in the disparity map, and displaying the disparity map to the diagnostician. Alternatively, the marking may be accomplished by forming a template from the disparity map and superimposing the template on one of the first and second ultrasonic images. Similarly, the disparity map may be formed with arrows from each point denoting a vector displacement of a point between the first and second ultrasonic images. The disparity map may then be overlaid over one of the first and second ultrasonic images or displayed directly a diagnostician. On the other hand, the disparity map may be formed from a magnitude of a vector disparity of a point between the first and second ultrasonic images and displayed as pixel intensities to the diagnostician.

Those skilled in the art will appreciate that the techniques of the invention may be implemented by providing EMT trained corpsmen with simple, hand-held scanners or "guns" that can be used in civilian emergencies or for military wounded, or used during transport of patients to the hospital. The techniques of the invention may also be used by trained hospital sonographers and physicians to improve the location and identification of tumors and foreign objects in the tissue of a patient. Other implementations of the invention will become apparent to those skilled in the art from the following detailed description of the invention.

BRIEF DESCRIPTION OF THE DRAWINGS

The foregoing and other novel features and advantages of the invention will become more apparent and more readily appreciated by those skilled in the art after consideration of the following description in conjunction with the associated drawings, of which:

FIG. 2 illustrates a N×N window located at $(x_i, y_j)$ in a first frame and displaced by a small amount in a second frame.

FIG. 3a illustrates the scatterer distribution of the tissue reflectivity $\rho(x)$ of uncompressed tissue.

FIG. 3b illustrates the scatterer distribution of the tissue reflectivity $\rho(x)$ of tissue after compression from the right.

FIG. 3c illustrates that displacement by $d_n$ aligns $\rho(x)$ and $\rho_c(x)$, where $d_n$ is the disparity at location $x_n$.

FIGS. 4a and 4b respectively illustrate the one-dimensional reflectivities of $\rho(x)$ and $\rho_c(x)$ before and after compression.

FIGS. 5a and 5b respectively illustrate the disparity d versus distance x from the anchor point at the origin for the case of small local inhomogeneities and where the local inhomogeneities dominate.

FIGS. 6a and 6b respectively illustrate the tissue displacement between two B-scan images induced by compression by a probe and by compression by natural breathing.

FIGS. 7a and 7b respectively illustrate a B-scan and a vector disparity map of a breast, where the B-scan of FIG. 7a is one of a pair of images, the second having been taken at a different time during a probe compression cycle than the B-scan of FIG. 7a.

FIG. 8 illustrates the disparity d versus sample number for a correlated binary sequence with arbitrary compressibilities α.

DETAILED DESCRIPTION OF THE PRESENTLY PREFERRED EMBODIMENTS

Figure 1A:
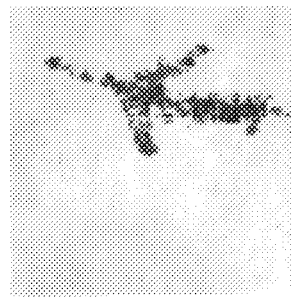
FIGS. 1a, 1b, 1c, and 1d respectively illustrate a high resolution radar image of a Boeing 727, the Boeing 727 of FIG. 1a in ground clutter, the Boeing 727 of FIG. 1b displaced by 3 pixels, and a two-dimensional disparity map of the images in FIGS. 1b and 1c.
Figure 1B:
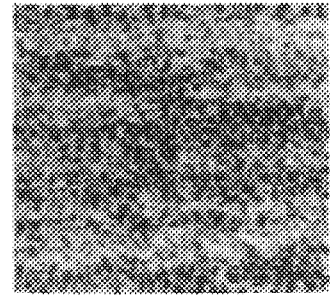
Figure 1C:
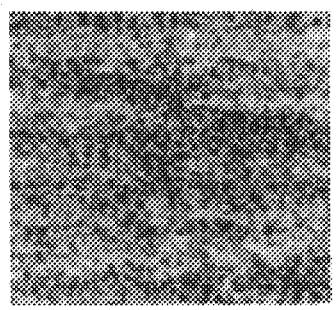

Preferred embodiments of the invention will now be described in detail with reference to FIGS. 1–15. Those skilled in the art will appreciate that the description given herein with respect to those figures is for exemplary purposes only and is not intended in any way to limit the scope of the invention. Those skilled in the art will also appreciate that while the description given herein is based on ultrasonic imaging the techniques of the invention also can be applied to electromagnetic and any other imaging methodology based on wave propagation from which similar speckle signature information may be obtained. All questions regarding the scope of the invention may be resolved by referring to the appended claims.

A DISPARITY MAPPER

In accordance with the invention, a disparity mapper detects and marks targets based on the differential distortion between targets and the background in pairs of 2-D images. As noted above, the present inventor previously found in radar testing that a disparity mapper dramatically reduced the amount of speckle and thereby increased contrast resolution. The contrast measure used in radar is called target-to-clutter ratio (TCR), and the disparity mapper was found to achieve target detection with a TCR as low as 0±3 dB (See, e.g., Perlow, "The Application of Stereoscopic Techniques to High Resolution Radar Images for Improved Visibility of Targets in Clutter," Ph.D. Dissertation, Univ. of Pennsylvania, 1994, and Perlow and Steinberg, "Automatic Stereo Processing of High Resolution Radar Imagery for Improved Visibility of Targets in Clutter," accepted by IEEE Trans. AES, April, 1995). These articles demonstrate the unusual detection sensitivity enhancement of a disparity mapper using radar images of weak targets in ground clutter. As will be explained in more detail below, this new ultrasound signal processor has the potential for detecting small, dense objects such as tumors and bits of shrapnel that would otherwise be obscured by speckle.

The disparity algorithm used in the radar experiments was a correlation-like approach to stereo matching. Such a method first selects a small, square window of size N×N pixels N typically 5 to 15) in the first image, as shown in FIG. 2, with a starting point ($x_0$, $y_0$) centered in the window. Equal size windows are then centered on the same point and all neighboring points in the second image. The correlation coefficients between the N×N pixel set in the first image and in each of the windows of the second image are then calculated. The vector displacement ($d_{00}$) that yields the highest correlation is noted and its numerical value is assigned to the element, at location ($x_0$, $y_0$), of a matrix called the disparity matrix. This displacement is called the disparity d at point ($x_0$, $y_0$). The next point ($x_1$, $y_0$) is then selected and the process is repeated, yielding element $d_{10}$ of the disparity matrix. The process is repeated for ($x_2$, $y_0$), etc., to ($x_F$, $y_F$), where F is the number of rows and columns in the frame, until the entire frame is processed. For each point ($x_n$, $y_j$) in the F×F frame the disparity $d_{ij}$ is measured. These new pixel values form the data matrix called the disparity matrix. Thus, referring to FIG. 2, the displacement giving the maximum correlation or minimum square difference between pixels within the windows discloses disparity $d_{ij}$, which is defined as the vector sum of $dx_i$ and $dy_j$.

Figure 1D:
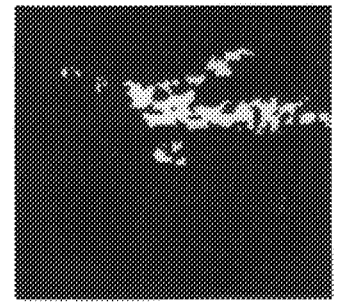

Horizontal displacement alone was used in the radar experiment, which corresponds to linear horizontal motion of the airplane between frames. Therefore the disparity values were only one dimensional correlation lags rather than vector displacements. To form the disparity map of the target as shown in FIG. 1d, all points that had disparity of 3 (corresponding to the horizontal target displacement between images) were painted white. All other points were painted black. The result is the extraordinarily high contrast, easily detectable target image of FIG. 1d, extracted by the disparity mapper from the relatively useless images of FIGS. 1b and 1c.

There are many variants of the disparity mapper algorithm, both in the similarity measure and in the formation of the output image. For example, the mean square difference between the windowed pixels also measures similarity and may be used instead of correlation. The main distinction between the two measures involves normalization of the total energies. Secondly, instead of painting the output image with disparity data, a template or mask can be formed from the disparity matrix that selects one or more disparity levels. The matrix elements describing the template is 1 for disparity values accepted and 0 for all others. The output image is the product of the input image and the template. On the other hand, the matrix elements of the template or mask describing the template may be 0 for disparity values accepted and 1 for all others, with the output image presented accordingly. Thirdly, a disparity map can be formed with arrows emanating from each point denoting the vector disparity, and the map can be overlaid on the B-scan image. Fourthly, the magnitude of the vector disparity between the respective B-scan images, being a scalar value, can be displayed as a pixel intensity between black and white. Examples of these techniques are described below.

ULTRASOUND MODEL

To explain how the above techniques have now been applied to ultrasound imaging, we begin by modeling tissue reflectivity ρ(x) as a set of point scatterers in two dimensions. Their amplitudes are $a_n$ and their locations are $x_n$, where x is the 2-D position coordinate ρ(x) can be written as:

$$\rho(x) = \sum_n a_n \delta(x - x_n) \quad \text{Equation (1)}$$

Equation (1) is pictured in one-dimension in FIG. 3a, which illustrates the scatterer distribution of the tissue reflectivity ρ(x) of uncompressed tissue. The far-field diffraction pattern as well as the near-field pattern observed by a focused transducer can be modeled by the Fourier transform of Equation (1). Therefore:

$$\rho(x) = \sum_n a_n \delta(x - x_n) \leftrightarrow p(u) = \sum_n a_n \exp(jkx_n u) \quad \text{Equation (2)}$$

where ←→ indicates Fourier pair and u=sinθsinφ is the angular coordinate in one dimension. In two dimensions, u is the 2-D angular coordinate with components u=sinθsinφ, v=sinθ cosφ, θ and φ being elevation and azimuth in polar coordinates. The summation is over index n. When a static compressive force is applied from the right, as in FIG. 3b, and the tissue is anchored at the origin, all scatterers are displaced to the left in proportion to their distances from the origin. The result is a change of scale by a compression scale factor $\alpha_n$, related to the mean compressibility of the tissue in the direction $x_n$ of the nth scatterer, altering Equation (1) to:

$$\rho_c(x) = \sum_n a_n \delta(x - \alpha_n x_n) \quad \text{Equation (3)}$$

In addition, local tissue inhomogeneities accumulate an additional displacement, $\delta x_n$, to each scatterer, modifying Equation (3), as depicted in FIG. 3b, and its Fourier transform to $$\rho_c(x) = \sum_n a_n \delta(x - \alpha_n x_n - \delta x_n) \leftrightarrow \rho_c(u) = \sum_n a_n \exp(jk[\alpha_n x_n + \delta x_n]u) \quad \text{Equation (4)}$$

The local perturbation in compression δx is assumed to be an uncorrelated, zero mean random variable. The disparity is that value of U that maximizes:

$$r(U, \Delta u) = \int_{U - \Delta u/2}^{U + \Delta u/2} p(u) p_c(u - U) du \quad \text{Equation (5)}$$

for window size Δu. r(U, Δu) is the vector disparity value.

While disparity r is defined in angular units, it can also be understood, interpreted and calculated as d, which was introduced earlier in linear units, as indicated in FIG. 2, in which the orthogonal displacements are given as δxi and δyj. The components of U in Equation (5) are U and V; they are related to δxi and δyj by δxi=UR and δyj=VR, where R is the focal distance of the transducer and also the distance to the tissue in the window. The disparity in linear units becomes that value of d that maximizes integral:

$$I = \int_{d - W/2}^{d + W/2} \rho(x) \rho_c(x - d) dx \quad \text{Equation (6)}$$

for window size W.

DISPARITY AND WINDOW SIZE

FIG. 4 depicts one-dimensional reflectivities ρ(x) and $\rho_c(x)$, before and after compression, respectively, where the anchor point is the origin. The nth scatterer is displaced from $x_n$ to $\alpha x_n + \delta x_n$. The size of the integration window is W. In this model, the disparity $o_n$ in the neighborhood of $x_n$ has two contributions: the first is the mean compression factor, $\alpha_n$, and the second is from the local perturbations in position $\delta x_n$ due to tissue inhomogeneities. Thus:

$$d_n = (1 - \alpha_n)x_n + \frac{1}{M} \sum_{m \text{ in } W}^{M} \delta x_m \qquad \text{Equation (7)}$$

where M is the number of scatterers in W. The first term is the expectation of $d_n$, $$Ed_n = (1 - \alpha_n)x_n$$

which is linear with the distance $x_n$ from the point at which the tissue is immobilized. The variance of d:

$$\text{var}(d) = \frac{1}{M} \text{var}(\delta x) = \frac{1}{M} \sigma_{\delta x}^2 \qquad \text{Equation (9)}$$

is independent of index n, permitting the dropping of the distance index. The standard deviation of d is $\sigma_d = M^{-\frac{1}{2}} \sigma_{\delta x}^2$.

FIG. 3c illustrates that displacement by $d_n$ aligns $\rho(x)$ and $\rho_c(x)$, where $d_n$ is the disparity at location $x_n$. Two models bound the variation of d with $x_n$ from the anchor point at the origin. In the first, the integration window W is large, implying large M and therefore small $\sigma_d$, and the first term in Equation (7) dominates. The limiting case is shown in one dimension in FIG. 5a, where the local inhomogeneities are small so that the constant slope dominates. There the second term vanishes and d rises linearly with x with slope $(1-\alpha)$. In the second model, the window W is small. As a consequence, M is small and $\sigma_d$ is large. Therefore, the second term in Equation (7) dominates. FIG. 5b shows the limiting case of small M, in which $d_n = \delta x_n$ and the local inhomogeneities dominate. The general case should fall somewhere in between.

Experiment shows that a second effect of window size is on the correlation distance of d, which grows with W, akin to the effect of the time constant of a lowpass filter. The lower limit on W is several times the speckle size in the B-scan to ensure a statistically significant measurement. The upper limit is several times smaller than tissue-bed size to ensure that the different compressibilities of adjacent types of tissue are not smoothed over by the integration window.

While a two-dimensional model is more complicated, it should nonetheless exhibit the same general longitudinal behavior. In addition, tissue can move transversely, in response to a longitudinal force, as well as longitudinally since it will displace along paths of least resistance. Experimental B-scan data are required as guides to modeling, and such experimental results will be described below.

EXPERIMENTAL PROCEDURE

An ultrasound probe was placed on the subject's breast in normal fashion, and the VCR was turned on for several seconds. Patient breathing provided the source of compression. In this way, a sequence of B-scans or frames could be obtained that covered several breathing cycles during which the probe was immobilized. Pairs of frames were selected at times of peaks of inhalation and exhalation. A portion of each selected frame was cropped at 160×160 pixel resolution and reformatted for Matlab, in which disparity calculations were made.

In addition to natural breathing, a second source of compression was through the probe itself. With the probe in contact with the skin, probe pressure was cyclically pressed into the breast and relaxed. Frame pairs were again selected and processed as just described.

The two modes are pictured in FIGS. 6a and 6b, where FIG. 6a illustrates tissue displacement between two B-scan images induced by a probe, while FIG. 6b illustrates the same for compression by natural breathing. As illustrated in FIG. 6a, probe compression depresses the surface under the probe and progressively less so away from it. The applied force is vertical and displaces tissue longitudinally down to the point of immobilization called the anchor, which is the chest wall. Tissue is also displaced transversely. In the idealized model the vector displacement is symmetric along the axis of the probe. Movement of the speckle pattern during a compression cycle follows tissue motion and therefore is also symmetric about the probe axis. The position of the moving probe is always the origin in a B-scan and, therefore, appears stationary. The anchor, on the other hand, if visible, appears to have maximum motion, notwithstanding the fact that it is immobilized. This is because its distance from the probe changes the most. The appearance is that of a compressive force applied to the anchor while the probe is immobilized. Disparity, therefore, should be zero at the origin and maximum at the anchor.

As shown in FIG. 6b, this is the same apparent motion when breathing is the compressive force because the probe always remains at the origin of an image. Physically, the probe is relatively stationary while the expanding and contracting lungs move the chest wall. In an idealized axially symmetric model a probe placed at position A would see symmetrical speckle motion similar to the probe compression case. In general, as at position B, the motion of the speckle pattern is asymmetric.

Shallow breathing, which is typical of mammography subjects during normal exams, generally provides insufficient displacement. Deep breathing, on the other hand, is often, but not always, satisfactory. Probe compression is the preferred procedure since it generally provides the most displacement.

DISPARITY EXPERIMENT ON SOFT TISSUE

Figure 7A:
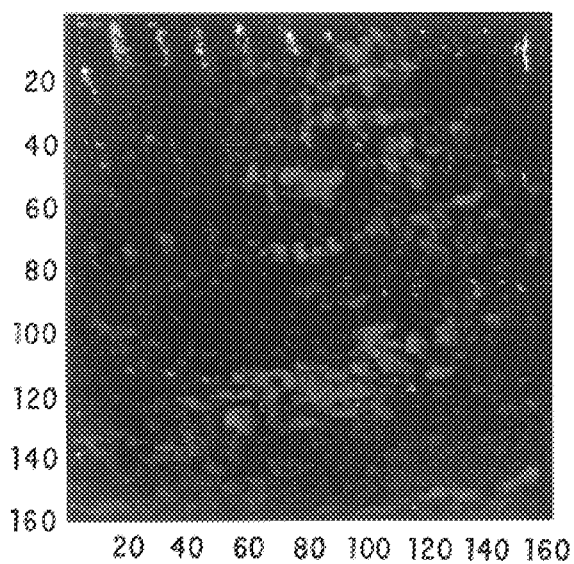

FIG. 7a illustrates a B-scan of a nontumorous male breast (upper half) with the chest wall and the lung below. The scanner used was an AI Performa, and the scale is 33 mm (160 pixels) from top to bottom. Some structure is seen at all depths, but the dominant characteristic throughout the image is speckle. A video recording was made of a sequence of such images as the skin surface upon which the ultrasound probe was placed was alternately compressed and relaxed. Recordings were also made of shallow and deep breathing. Probe location is the top center of the image. A pair of B-scans half a second apart was selected, of which FIG. 7a is one. Because the tissue is primarily soft tissue and has no abnormalities, no large scale disparity patterns significantly different from neighboring regions would be expected.

Figure 7B:
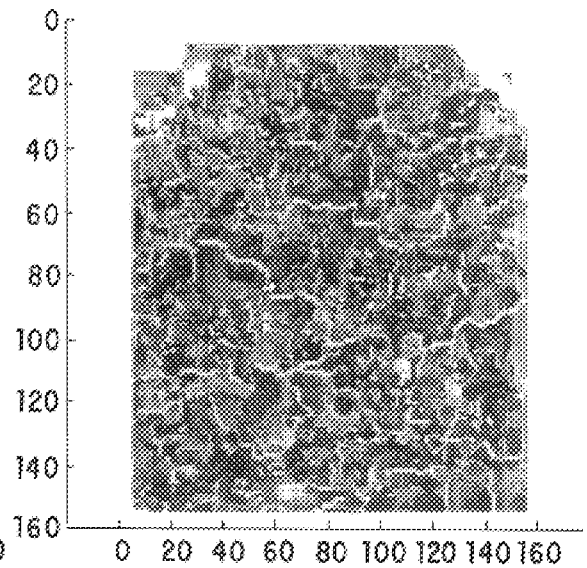

FIG. 7b is the disparity map made from the in vivo scans at a different time during the probe compression cycle. W=9 pixels. The short strokes with arrowheads give the magnitudes and vector orientations of the disparity at each point. There is no pattern evident. The disparity appears random, as would be expected for soft tissue. The anchor is somewhat below the bottom of the picture. If the linear compression was not dominated by local perturbations, the disparity would increase from top to bottom. Some evidence of this happening was found, by measurement at each depth, and the vertical component of disparity averaged from 60<x<80, for W=5, 9 and 17. The abscissa interval (60, 80) was about 1 cm, located directly below the 2-cm probe. The curves exhibited a mean negative slope of one disparity unit per 150 pixels. Also the lowpass filtering effect with increasing W was apparent. Good disparity data was obtained with probe compression; however, useful data could not be obtained closer than 50–70 pixels from the surface.

The discrete structure in the disparity map of FIG. 7b is somewhat deceiving; it is more an artifact of the disparity process and less a characteristic of the tissue. The disparity calculation tends to sharpen edges and boundaries, much like median filtering. As the window (FIG. 2) moves from a low toward a high disparity region, the disparity estimate d switches abruptly as the balance from low to high changes. FIG. 8 is a simulation showing this behavior. In FIG. 8, a one-dimensional uncompressed data sample was a correlated binary sequence consisting of runs of 0s and 1s. Arbitrary compression coefficients were assigned each run to form the compressed sequence. The abrupt disparity "switching" is evident from FIG. 8.

DENSE TISSUE AND SOLID OBJECTS

As noted above, the present invention began as an attempt to distinguish small tumors from healthy tissue. For the technique to be considered a success, a dense tumor should be differentiated from soft tissue and marked, based on their relative speckle signatures. Not only must such targets be marked by the technique of the invention, but soft tissue should remain unmarked. The importance of the experiment above is that it demonstrates that soft tissue is not marked.

All the remaining B-scans were taken of female mammography patients with tumors. Compression was affected by normal breathing. The better procedure, probe compression, was not possible. Thus, the only source of motion was shallow breathing by the subject, which is much less effective. An exception was a disparity experiment with a biopsy needle in which needle motion induced the tissue displacement. The frames were selected from a video made by Acoustic Imaging illustrating ultrasound needle-guided biopsy. The equipment was an AI Performa.

Figure 9A:
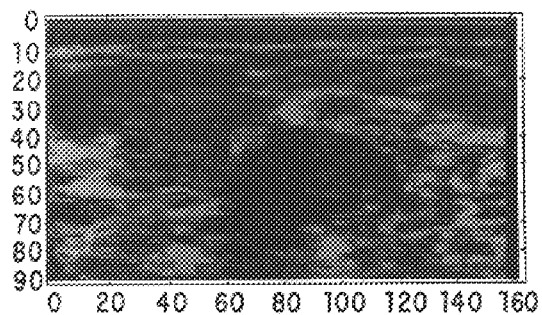
FIGS. 9a and 9b illustrate B-scans of a female breast showing a central tumor plus lights and darks characteristic of speckle under the condition of natural breathing.
Figure 9B:
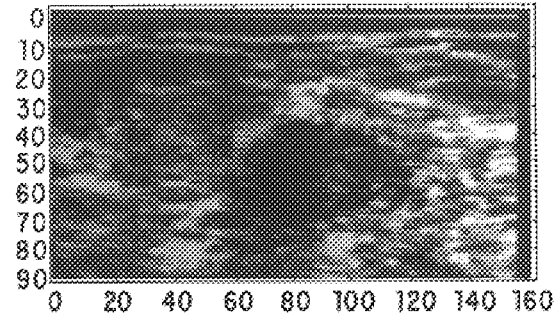

FIGS. 9a and 9b illustrate in vivo B-scan images of female breast tissue taken 1 second apart. The dark central oval is a tumor, and the hypoechogenic region in the upper left, between ordinates 20 and 40, is suspicious. Much of the remaining "patterns" are speckle artifacts. While the differences between FIGS. 9a and 9b are barely visible, the disparity mapper created a disparity map (FIG. 9c) which, when overlaid on the image (FIG. 9d) was able to perceive the differences and mark the tumor.

Figure 9C:
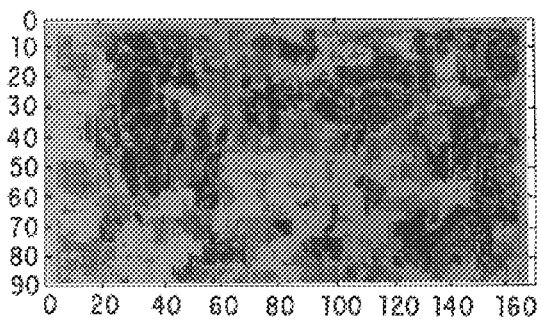
FIGS. 9c and 9d respectively illustrate a disparity map and the image of FIG. 9a overlaid with the disparity data of FIG. 9c to mark the tumor.
Figure 9D:
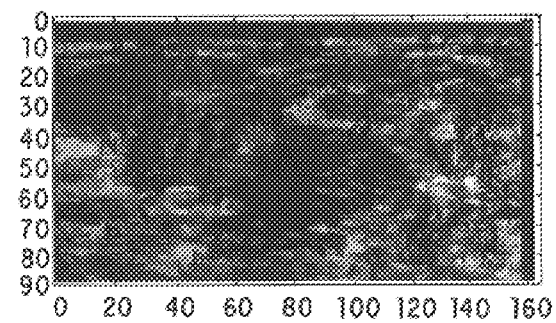

FIG. 9c shows the vector disparity map of FIGS. 9a and 9b, and FIG. 9d is an overlay of the disparity map of FIG. 9c on the B-scan. The scale from top to bottom is 4 cm. The resolution is 160×160 pixels. The tumor is ringed by what looks like "shear" at the edges of the tumor, which helps to accentuate the tumor. The upper left "suspicious" region was marked, as well as two other small regions near the upper right of the tumor. The shear is probably due to differential strain between dense tumor tissue and less dense surrounding tissue in response to the stress variations induced by breathing. Shear data may relate to relative compressibility of tissue types and therefore may be clinically informative.

Figure 10:
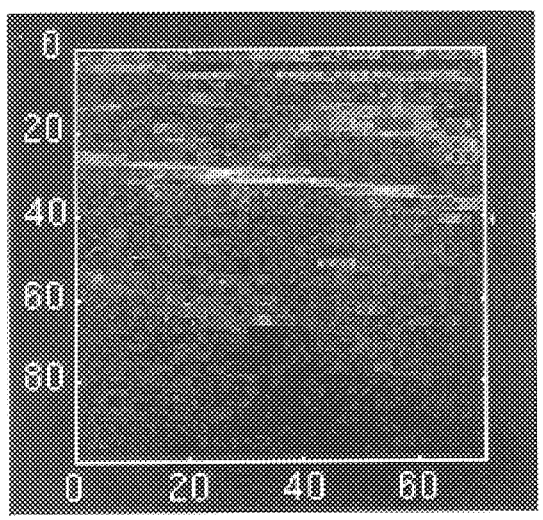
FIG. 10 illustrates a B-scan image of a breast in which a biopsy needle is visible.

A different disparity display was used in a second tumor experiment, also showing detection by marking. The map is in template format rather than as disparity arrows. In this way, a narrow range of disparity values can be selected for display, much as a filter selects a narrow band of frequencies from a broad spectrum. The disparity matrix of vector disparities was formed as described above. The horizontal components of the disparities (the $\delta x_i$ in FIG. 2) at each point were used in the experiment. The selected values were 0 and ±1, which centered the disparity filter on the tumor-tissue value. To form the disparity map all points that had disparity values of 0 and ±1 were unpainted. All other points were painted white. The map, therefore, is a template or cut-out. The resolution is 80×80 pixels. FIG. 10 is one of the pair of female in vivo breast images formed in this manner for a natural breathing patient, where about 1 second separated the frames. The tumor is the central dark area extending upward and toward the right. A biopsy needle pierces the tumor from the left and is visible in the upper half of each image.

Figure 11:
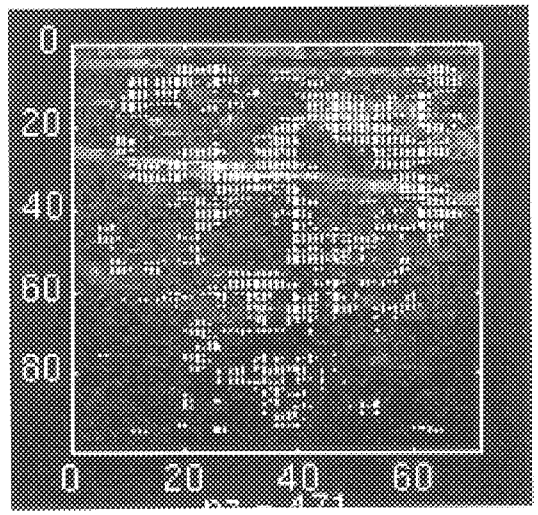
FIG. 11 illustrates an overlay of a one-dimensional scalar disparity template on the B-scan of FIG. 10, showing the tumor outlined by the template in the upper half of the image. The compression is induced only by natural breathing.

The template overlaid on the B-scan image of FIG. 10 is shown in FIG. 11. All pixels with disparity 0 and ±1 are unchanged and all other pixels are overwritten. The result is instant marking of the upper and lower poles of the tumor in the upper half of the image by the white painting around it. The needle and the soft tissue are both differentiated from the tumor but not from each other because they both fall into the category of "not 0 or ±1". The break in the needle in the overlay seen between abscissa values of 45 and 55 is accounted for by a break in continuity in reflectivity of the needle in the second B-scan image.

Figure 12A:
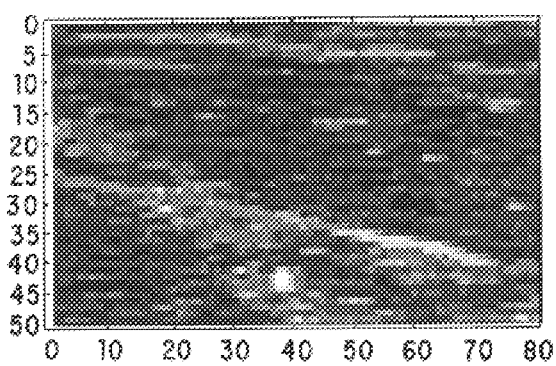
FIGS. 12a and 12b respectively illustrate a biopsy needle and the disparity data for the biopsy needle plotted as pixel intensities, showing that the affected tissue mass surrounding the biopsy needle is 50 times larger than the biopsy needle.
Figure 12B:
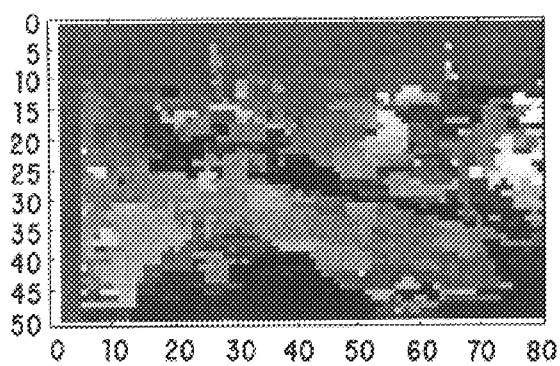

Given that the method marked dense tumorous tissue it is reasonable to expect that it would mark compact, solid targets such as small metal parts (shrapnel). Images of the ultrasound needle in the experiment above are believed to be illustrative of this. As seen in the upper half of FIG. 10, the needle's length makes it easily visible, running approximately horizontally from ordinate values of about 25 to 40, but gives it unrealistic disparity values because it has edges only. Accordingly, as shown in FIGS. 12a and 12b, two B-scans were again spaced by 1 second. A biopsy gun was fired between B-scans. The scale is 4 cm from top to bottom. The disparity template, where the data is plotted as pixel intensities "tuned" to the needle, is seen in reversed polarity in FIG. 12a. The needle stands out clearly. As can be appreciated from FIG. 12b, the disparity image indicates that the affected tissue mass surrounding the needle is approximately 50 times larger than the needle.

Figure 13:
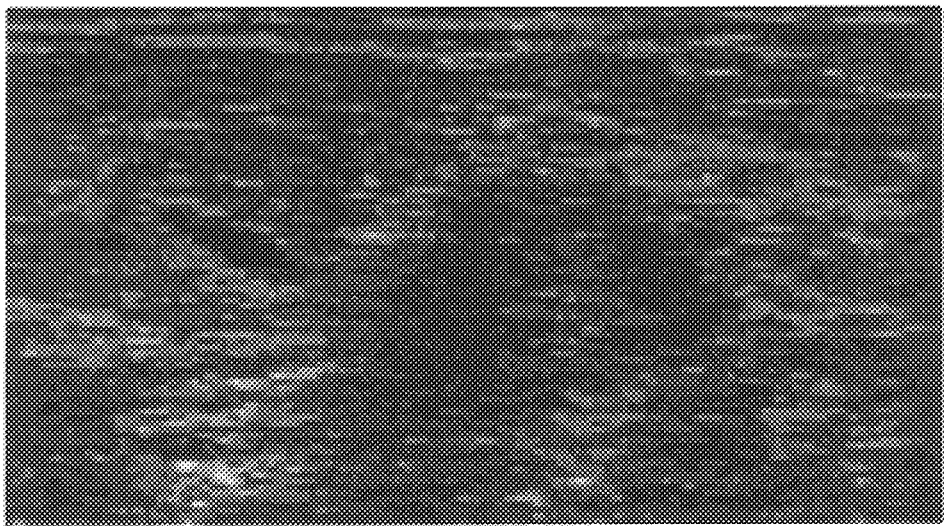
FIG. 13 illustrates in the upper left a wake of entrapped body fluids or air in tissue following removal of a biopsy needle.
Figure 14:
FIG. 14 illustrates the wake of FIG. 13 after three seconds have elapsed, showing that the wake is hardly visible.
Figure 15:
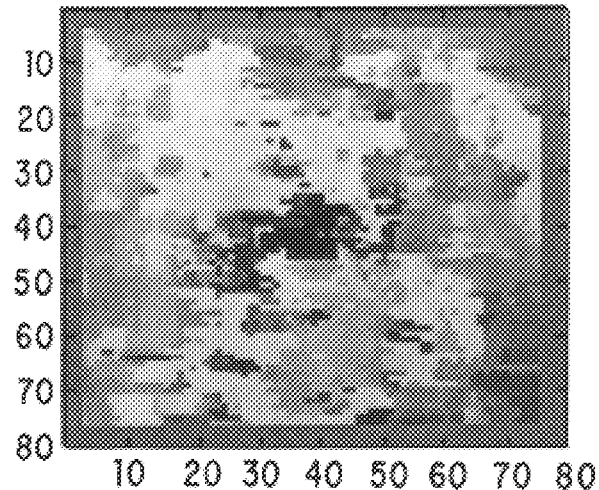
FIG. 15 illustrates a disparity map of the image of FIG. 14.

A small section of data in which a needle is withdrawn, leaving a "wake" of entrapped body fluids or air, as might exist in the body following penetration by a small rigid part, was also examined. The upper left of FIG. 13 shows a B-scan with such a wake near a tumor. The wake is black and easily visible, at a 45 degree slope and pointed toward the tumor. FIG. 14 illustrates the same scene 3 seconds later, from the same sequence of frames, when the wake had begun to close. It is a more severe test because the wake is hardly visible. In FIG. 15, the disparity map of the FIG. 14 data clearly marks this wake.

Accordingly, the experimental results show that dense clusters of tumor cells may be distinguished from soft tissue by disparity mapping. By contrast, the soft tissue experiment resulted in no marking. Also, when a long metal biopsy needle is embedded in soft tissue plus tumor and the disparity filtering is "tuned" for a tumor, the tumor alone is marked. This evidences that the technique of the invention is highly suitable for the proposed function of detection and marking of small compact objects in the body. Moreover, a wake of trapped air or clear body fluid caused by a penetrating body is discernable by disparity mapping.

The method of the invention thus offers a way to materially improve detectability of dense tissue and other materials. Its value lies in rapid discrimination between soft tissue and tumors as well as shrapnel and other small rigid parts. Those skilled in the art will appreciate that the technique of the invention may be used by EMT trained corpsmen with simple, hand-held scanners or "guns" that can be used in civilian emergencies or for military wounded, or used during transport of patients to the hospital. The method of the invention may also be used by trained hospital sonographers and physicians. Other implementations will be apparent to those skilled in the art from the foregoing description.

Although several embodiments of the invention have been described in detail above, those skilled in the art will appreciate that numerous other modifications to the invention are possible within the scope of the invention.

Accordingly, the scope of the invention is not intended to be limited to the preferred embodiments described above, but only by the appended claims.

I claim:

1. A method of identifying tumors and foreign materials in soft tissue of a patient using ultrasound imaging, comprising the steps of:
   a. imaging a target soft tissue area to obtain a first ultrasonic image;
   b. displacing said target soft tissue area;
   c. imaging said displaced target soft tissue area to obtain a second ultrasonic image; and
   d. identifying whether tumors or foreign materials are present in said target soft tissue area based on changes in a speckle pattern between said first and second ultrasonic images.

2. A method as in claim 1, wherein said displacing step comprises the step of compressing said target soft tissue area with a probe.

3. A method as in claim 1, wherein said target soft tissue area comprises a patient's breast tissue and said displacing step comprises the step of waiting a predetermined interval of time during the patient's breath cycle whereby displacement of said breast tissue is caused by the patient's breath cycle.

4. A method as in claim 1, wherein said identifying step comprises the step of generating a disparity map of speckle signatures of said first and second ultrasonic images and marking said tumors or foreign materials in one of said first and second images using said disparity map.

5. A method as in claim 4, wherein said identifying step comprises the step of marking points displaced between said first and second ultrasonic images with a first pixel intensity in said disparity map, marking points which are minimally displaced between said first and second ultrasonic images with a second pixel intensity in said disparity map, and displaying said disparity map to a diagnostician.

6. A method as in claim 4, wherein said identifying step comprises the steps of forming a template from said disparity map and superimposing said template on one of said first and second ultrasonic images.

7. A method as in claim 4, wherein said identifying step comprises the steps of forming said disparity map with arrows from each point denoting a vector displacement of a point between said first and second ultrasonic images and overlaying said disparity map over one of said first and second ultrasonic images.

8. A method as in claim 4, wherein said identifying step comprises the steps of forming said disparity map from a magnitude of a vector disparity of a point between said first and second ultrasonic images and displaying said disparity map as pixel intensities to a diagnostician.

9. A method as in claim 1, wherein said identifying step comprises the steps generating a disparity map of speckle signatures of said first and second ultrasonic images with arrows from each point denoting a vector displacement of a point between said first and second ultrasonic images and displaying said disparity map to a diagnostician..

* * * * *